US010987020B2

(12) United States Patent
Weiss et al.

(10) Patent No.: US 10,987,020 B2
(45) Date of Patent: Apr. 27, 2021

(54) METHOD FOR TISSUE CLASSIFICATION, COMPUTER PROGRAM PRODUCT AND MAGNETIC RESONANCE IMAGING SYSTEM

(71) Applicant: KONINKLIJKE PHILIPS N.V., Eindhoven (NL)

(72) Inventors: Steffen Weiss, Eindhoven (NL); Ulrich Katscher, Eindhoven (NL); Christian Stehning, Eindhoven (NL); Michael Gunter Helle, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 401 days.

(21) Appl. No.: 15/772,149

(22) PCT Filed: Oct. 17, 2016

(86) PCT No.: PCT/EP2016/074841
§ 371 (c)(1),
(2) Date: Apr. 30, 2018

(87) PCT Pub. No.: WO2017/076618
PCT Pub. Date: May 11, 2017

(65) Prior Publication Data
US 2018/0310856 A1    Nov. 1, 2018

(30) Foreign Application Priority Data

Nov. 2, 2015    (EP) .................................... 15192594

(51) Int. Cl.
*A61B 5/055* (2006.01)
*A61B 5/107* (2006.01)
(Continued)

(52) U.S. Cl.
CPC ............ *A61B 5/055* (2013.01); *A61B 5/1075* (2013.01); *G01R 33/5608* (2013.01);
(Continued)

(58) Field of Classification Search
CPC .. A61B 5/055; A61B 5/1075; G01R 33/5608; G01R 33/481; G01R 33/4812;
(Continued)

(56) References Cited

U.S. PATENT DOCUMENTS 6,466,813 B1    10/2002  Shukla et al.
2009/0187098 A1*  7/2009  Makower ......... A61B 17/12022
                                                600/424
(Continued)

FOREIGN PATENT DOCUMENTS

WO    2013001399 A2    1/2013
WO    2014161766 A1    10/2014

OTHER PUBLICATIONS

Brandao et al, Comparing T1-weighted and T2-weighted three-point Dixon technique with conventional T1-weighted fat-saturation and short-tau inversion recovery (STIR) techniques for the study of the lumbar spine in a short-bore MRI machine, Clinical Radiology 68 (2013) 617-623 (Year: 2013).*
(Continued)

*Primary Examiner* — Amelie R Davis
*Assistant Examiner* — John Denny Li
(74) *Attorney, Agent, or Firm* — Sherry Austin

(57) ABSTRACT

It is an object of the invention to improve tissue classification in MRI images. In particular it is an object of the invention to improve the classification of bone and air in MRI images. This object is achieved by a method for tissue classification in a region of interest in a magnetic resonance (MR) image comprising a first region and a second region, wherein the first region represents air and the second region
(Continued)

represents bone. The method comprises the steps of: —acquiring a first magnetic resonance image comprising the first and the second region and; —acquiring a second magnetic resonance image comprising the first and the second region, wherein the first region has a different shape in the second magnetic resonance image compared to the first magnetic resonance image and; —identifying the first region and second region in the first and second image and; —comparing the first image and the second image with respect to the first region and the second region and; —classifying the first region as region representing air based on a presence of a shape difference between the first and the second image and classifying the second region as bone based on an absence of the shape difference between the first and second image.

18 Claims, 2 Drawing Sheets

(51) Int. Cl.
  *G01R 33/56* (2006.01)
  *G06T 7/00* (2017.01)
  *G01R 33/48* (2006.01)
(52) U.S. Cl.
  CPC .......... *G06T 7/0014* (2013.01); *G01R 33/481* (2013.01); *G01R 33/4812* (2013.01); *G06T 2207/10088* (2013.01); *G06T 2207/20081* (2013.01); *G06T 2207/20104* (2013.01); *G06T 2207/30008* (2013.01)
(58) Field of Classification Search
  CPC ......... G01T 7/0014; G01T 2207/10088; G01T 33/20081; G01T 33/20104; G01T 33/30008
  See application file for complete search history.

(56) References Cited

U.S. PATENT DOCUMENTS

| | | | |
|---|---|---|---|
| 2011/0286649 A1* | 11/2011 | Reisman | G01R 33/4812 382/131 |
| 2013/0197888 A1* | 8/2013 | Hart | G06F 19/30 703/6 |
| 2014/0161334 A1* | 6/2014 | Wang | G06T 7/12 382/131 |

OTHER PUBLICATIONS

Boettger et al., Radiation therapy planning and simulation with magnetic resonance images, Medical Imaging 2008 (Year: 2008).*
Nyholm et al "Counterpoint: Opportunities and Challenges of a Magnetic Resonance Imaging—Only Radiotherapy Workflow" Seminars in Radiation Oncology, 2014, p. 175-179.
Stanley et al "Automated Classification of Bone and Air Volumes for Hybrid PET-MRI Brain Imaging" 2013 International Conference on Digital Image Computing . . . Nov. 26, 2013, p. 1-8.
Khateri et al "Generation of Attenuation Map for MR-Based Attenuation Correction of Pet Data in the Head Area Employing 3D Short Echo Time MR Imaging" Nuclear Instruments& Methods in Physics Research, . . . vol. 702, Feb. 1, 2013 p. 133-136.
Buerger C et al. Investigation of MR-Based Attenuation Correction and Motion Compensation for Hybrid PET/MR IEEE Trans. Nucl. Science 2012;59:1967-1976.
Fatterpekar GM et al. "Imaging the Paranasal Sinuses: Where We Are and Where We Are Going" The Anatomical Record 2008;291:1564-1572.
Halléen H, Juto JE. "Nasal mucosa reaction. A model for mucosal reaction during challenge" Rhinology 1992;30(2):129-33.
Gerth van Wijk R, Dieges PH. Nasal hyper-responsiveness to histamine, methacholine and phentolamine in patients with perennial non-allergic rhinitis and in patients with infectious rhinitis. Clin Otolaryngol 1991;16(2):133-7.
Stanescu et al "3T MR-based Treatment Planning for Radiotherapy of Brain Lesions" Radiol. Oncol. 2006 40(2) p. 125-32.
Stanescu et al, "A Study on the Magnetic Resonance Imaging (MRI) Based Radiation Treatment Planning of Intracranial Lesions" Phys. Med. Biol. 53 (2008) p. 3579-3593.
Edmund et al "Auto-Segmentation of Bone in MRI-Only Based Radiotherapy Using Ultra Short Echo Time" Radiotherapy and Oncology vol. 103, Supplement 1, May 2012, p. S75.
Karotki et al "Comparision of Bulk Electron Density and Voxel Based Electron Density Treatment Planning" Journal fo Applied Clinical Medical Physics, vol. 12, No. 4, Fall, 2011.
Dowling et al "An Atlas Based Electron Density Mapping Method for Magnetic Resonance Imaging (MRI) Alone Treatment Planning and Adaptive MRI-Based Prostate Radiation Therapy" Int J Radiation Oncol Biol Phys, vol. 83, No. 1, pp. e5ee11, 2012.
Devic: "MRI-Simulation for RTP" Medical Physics, vol. 39, No. 11, Nov. 2012.
Jonsson et al "Treatment Planning Using MRI Data: An Analysis of the Dose Calculation Accuracy for Different Treatment Regions" Radiation Oncology, 2010 5:62.

* cited by examiner

METHOD FOR TISSUE CLASSIFICATION, COMPUTER PROGRAM PRODUCT AND MAGNETIC RESONANCE IMAGING SYSTEM

CROSS REFERENCE TO RELATED APPLICATIONS

This application is a U.S. national phase application of International Application No. PCT/EP2016/074841, filed on Oct. 17, 2016, which claims the benefit of EP Application Serial No. 15192594.8 filed on Nov. 2, 2015 and is incorporated herein by reference.

FIELD OF THE INVENTION

The invention relates to the field of magnetic resonance imaging (MRI) and more specifically to an MRI system and computer program product for use in MRI systems. The invention further relates to the field of image processing of magnetic resonance images.

BACKGROUND OF THE INVENTION

Attenuation maps for use in radiation therapy are conventionally derived from computed tomography scans since the CT values (Hounsfield values) directly relate to attenuation of radiation. Also, CT images readily provide tissue classification into bone, soft tissue, fat, and air. However, they expose the subject to ionizing radiation, and often, magnetic resonance imaging (MRI) is superior to visualize the tumor and risk organs. However, MR-based simulation of attenuation maps is difficult, since there is no type of MR contrast available that depends on radiation attenuation. It is subject of current research, which combination of MR contrasts/image types and which image processing algorithms are most suitable for simulation of CT images and attenuation maps. An overview of opportunities and challenges in this field is given by Nyholm, T and Jonsson J, Counterpoint: Opportunities and Challenges of a Magnetic Resonance Imaging—Only Radiotherapy WorkFlow, Seminars in Radiation Oncology, 2014, pages 175-179.

One major problem in MRI-only-based RT planning especially in the head neck region is to differentiate between bone (in particular cortical bone) and air, which are both hypo-intense in MRI.

US2011/0286649 describes a method for generating a pseudo CT image based on two UTE images. Trained classifiers are used to segment bone. A first UTE image is acquired with a lower TE than a second UTE image. The first UTE image can therefore be blurry. The blur region may be eroded slightly via morphological methods. The eroded head mask in the first UTE image may then be compared with the eroded head mask in the second UTE image. The blur region may then be defined as the as that part of the eroded first UTE image which the head mask in the second UTE image defines as background. The blur region may then be removed from the first UTE image head mask to generate a final head mask.

SUMMARY OF THE INVENTION

It is an object of the invention to improve tissue classification in MRI images. In particular it is an object of the invention to improve the classification of bone and air in MRI images. According to a first aspect of the invention this object is achieved by a method according to claim 1. According to a second aspect of the invention this object is achieved by a computer program product according to claim 6. According to a third aspect of the invention this object is achieved by an MRI system according to claim 7.

Bone tissue is a rigid tissue, which in general does not change shape easily, whereas air cavities inside the body can more easily change shape. It is an insight of the inventors that this knowledge can be exploited to distinguish between bone and air in MRI images. If a shape change occurs in the air cavities, this change in shape can be exploited by comparing an image acquired prior to the shape change (the first image) and an image acquired after the shape change (the second image). A low signal intensity region affected by the shape change can be classified as air, whereas a low signal intensity region which is not affected by the shape change can be classified as bone. Hereby tissue classification can be improved. Throughout this application, the first region represents air and the second region represents bone.

According to embodiments of the invention the shape difference of the first region is caused by a change in a third region. This third region could for example be mucosa and the change could be a thickening of this mucosa, e.g. in the head and neck area. According to further embodiments of the invention, the shape change is induced. Actively inducing the shape change is advantageous, because in this way the shape change may be better controllable. The shape change could for example be induced by administration of histamine, methacholine or phenotolamine for example in the case of head and neck imaging. Administration of histamine, methacholine or phenotolamine affects the mucosa thickness present in the head and neck area. Mucosa thickens only in the direction of the air cavity and thereby, by comparing the first and second magnetic resonance image, it is possible to distinguish between bone and air. The opposite situation can also be used for tissue classification. For example, some patients suffer from nasal allergy. In these patients the mucosa thickness may have been decreased between the first and second magnetic resonance image by means of administration of an anti-histamine drug.

However, the shape change does not necessarily have to be induced. Shape changes could also just happen over time. In this case one could just wait for the shape change to happen. For example, a passage of stool through a bowel could also affect the shape of air cavities present. Also, breathing could induce a shape change. So, the change in shape can be induced in many different ways. The invention is based on the insight that this shape change can be exploited for image processing and tissue classification.

According to embodiments of the invention a pseudo CT image and/or an attenuation map and/or a digitally reconstructed radiograph (DRR) of the region of interest can be generated based on the tissue classification. This is advantageous, because the pseudo CT image and/or the attenuation map and/or the DRR can be used by an MRI system comprising a radiotherapy delivery system to generate a radiotherapy plan. Also the pseudo CT image and/or the attenuation map and/or the DRR can be used by an MRI system comprising a PET system to create an attenuation map in order to correct PET images.

Method steps of the invention can be implemented in program code means of a computer program product. This computer program product could be a stand alone program configured for tissue classification on magnetic resonance images. Also the computer program product could be integrated into an MRI system. The MRI system could be configured to acquire the first and second magnetic resonance image and performing a tissue classification by exploiting the information that air may change shape over time, whereas bone does not change shape over time. This is especially advantageous if the MRI system is combined with either a radiotherapy delivery system or PET system, because in these cases the tissue classifications can be used in (online) radiotherapy plan calculations used by the radiotherapy delivery system or attenuation corrections used by the PET system.

These and other aspects of the invention will be apparent from and elucidated with reference to the embodiments described hereinafter.

DETAILED DESCRIPTION OF EMBODIMENTS

Figure 1:
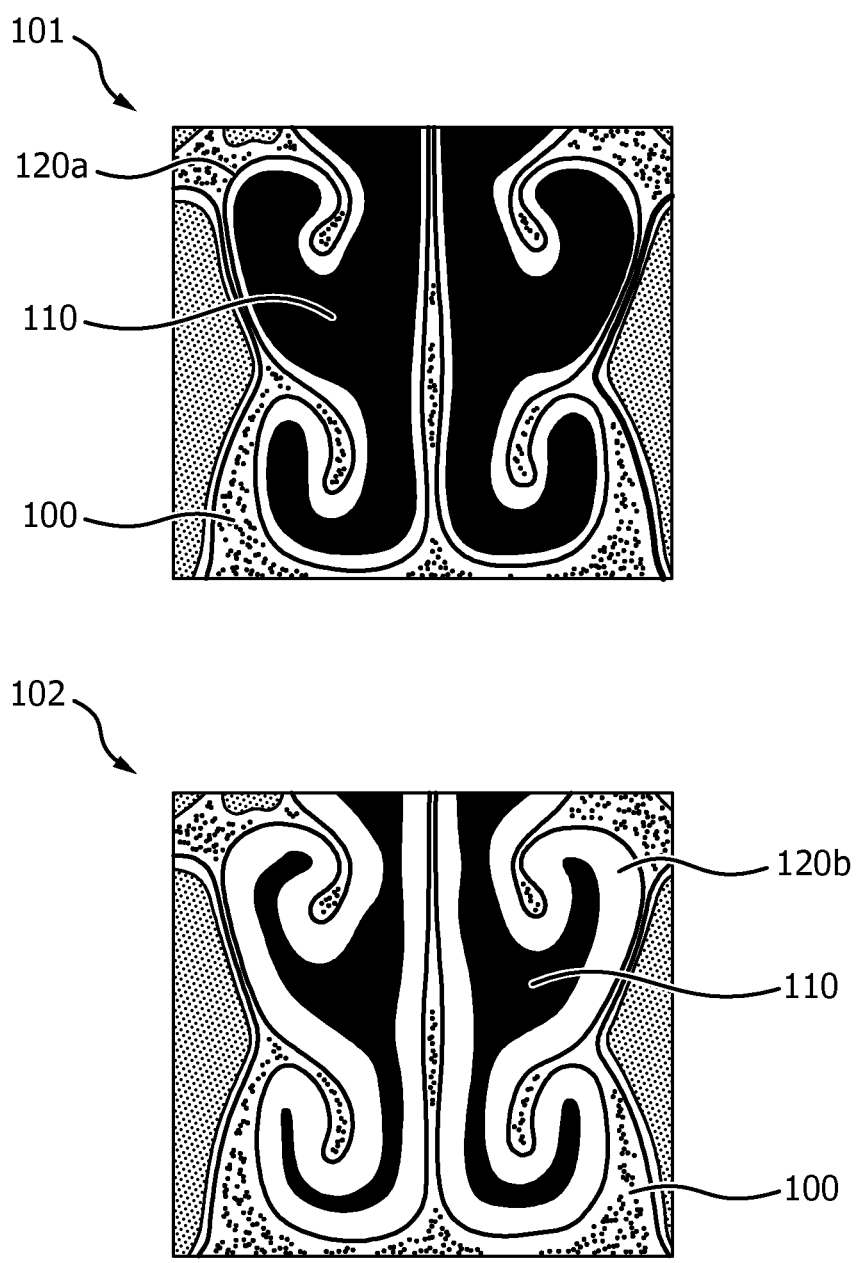
FIG. 1 shows a drawing of a head an neck region, in particular the nasal lobes

FIG. 1 diagrammatically shows a drawing of a head and neck region in particular the nasal lobes. This figure shows bone tissue 100 and air 110. The left subfigure 101 is a representation of a situation before an induced change in the mucosa 120 and thereby in air 110. The right subfigure 102 is a representation of a situation after an induced change (e.g. administration of histamine, methacholine or phenotolamine). As a result mucosa 120 is thicker 120b in the right image compared to the left image 120a.

In general air-filled cavities of the head neck region are surrounded by mucosa tissue 120. In other words, the mucosa represents an intermediate layer between air 110 and bone 100. It is possible to induce substantial thickness changes of the mucosa. Since the bone structures are rigid, a thickness increase of the mucosa can only be realized by extending towards air cavity. This can be used to differentiate between air and bone tissue in MRI images.

Figure 2:
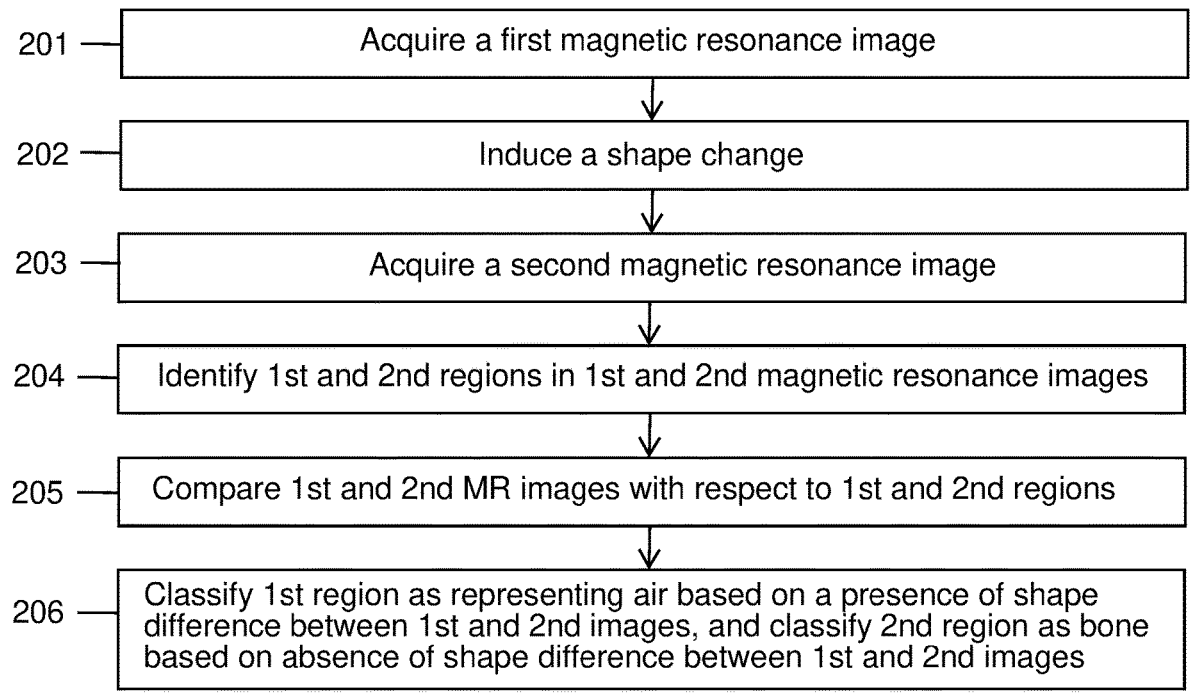
FIG. 2 shows a flow diagram of a method according to the invention and FIG. 3 diagrammatically shows a magnetic resonance imaging system according to the invention.

FIG. 2 shows a flow diagram of a method according to the invention.

Step 1: Acquiring a first magnetic resonance image 201, wherein the first magnetic resonance image comprises the first region 110 and the second region 100.

Step 2: Induce a shape change in a third tissue with predetermined tissue type 202. In this case the third tissue is mucosa 120.

Step 3: Acquiring a second magnetic resonance image 203, wherein the second magnetic resonance image comprises the first region 110 and the second region 100. In the second magnetic resonance image, the mucosa and thereby the first region has a changed shape compared to the first magnetic resonance image. Optionally, the first and second magnetic resonance image can be registered to compensate for residual errors caused by patient movement.

Step 4: Identifying the first and second region in the first and second magnetic resonance image 204. This could for example be achieved by classifying all voxels within a representation of a patient in the first and second magnetic resonance image that show noise level intensity as "first or second region" or "bone or air".

Step 5: Comparing the first and second magnetic resonance image with respect to the first and second region 205.

Step 6: classifying the first region as region representing air based on a presence of a shape difference between the first and the second image and classifying the second region as bone based on an absence of the shape difference between the first and second image 206. This could for example be achieved in the following way. Classify those pixels as air that change from noise level intensity in the first magnetic resonance image to standard mucosal signal level in the second magnetic resonance image. Apply region growing algorithm to pixels classified as air in the first magnetic resonance image to classify all remaining air pixels. Classify all remaining pixels on noise level intensity in the first image as bone pixels.

Those skilled in the art will understand that some steps of the method are interchangeable. For example one can identify the first and second region in the first magnetic resonance image before acquiring the second magnetic resonance image. Further, for example one could first detect the shape change between the first and second magnetic resonance image (e.g. by detecting a change in signal intensity between corresponding voxels in the first and second magnetic resonance image) before identifying the first and second region. Other chronological changes in step order are possible. However, the shape change needs to be in between the acquisition of the first and second magnetic resonance image.

A favourable way of acquiring the first and second image is by means of a T1w Dixon sequence. T1w DIXON scans have been shown to allow for differentiation of water-type and fat-type tissues. The data acquisition can be achieved with a clinical MRI system (FIG. 3, 300) using the body coil for transmission, and, for instance, a 12-element phased-array posterior coil and a 16-element phased-array anterior coil for signal reception. A T1-enhanced 3D Cartesian fast-field echo acquisition is employed, acquiring two signal echoes with the magnetization nearly out-phase at $TE_1=1.1$ ms and nearly in-phase at $TE_2=2.1$ ms. Other imaging parameters can be e.g. repetition time TR=3.3 ms, flip angle $\alpha=10°$, voxel size $1.7\times1.7\times2.5$ mm$^3$, FOV $300\times400\times350$ mm$^3$.

As initial step, air and bone is identified as far as possible with standard medical image processing (e.g., mouth, ears in case of head and neck region). Remaining hypo-intense image regions are identified, yielding N regions which have to be classified as air or bone. It is assumed that all air and bone regions are separated by non-void areas, i.e., each identified hypo-intense region contains exclusively air or bone. The N hypo-intense regions are identified on both the first and second image, and the corresponding volumes $V_{ni}$ are determined, where index i represents the first or second image, and index n ($1 \leq n \leq N$) represents the different hypo-intense regions. Region n is classified as air if $|V_{an}-V_{bn}|/0.5(V_{an}+V_{bn})>T$ i.e., the (normalized) volume change of region n is larger than a certain threshold T, indicating the impact of changing mucosa. On the other hand, region n is classified as bone if $$\frac{|V_{an} - V_{bn}|}{0.5(V_{an} + V_{bn})} < T$$

i.e., the observed change of region volume is too small, and was not affected by changing mucosa.

The method steps can be implemented in a computer program product. This computer program product could be a product configured for tissue classification. In this case the first and second magnetic resonance image are received by the computer program product, after which the computer program product is configured to perform method steps 4-6.

Also the computer program product could be incorporated into an MRI system. In those cases method steps 1 and 3-6 can be performed by the computer program product.

Figure 3:
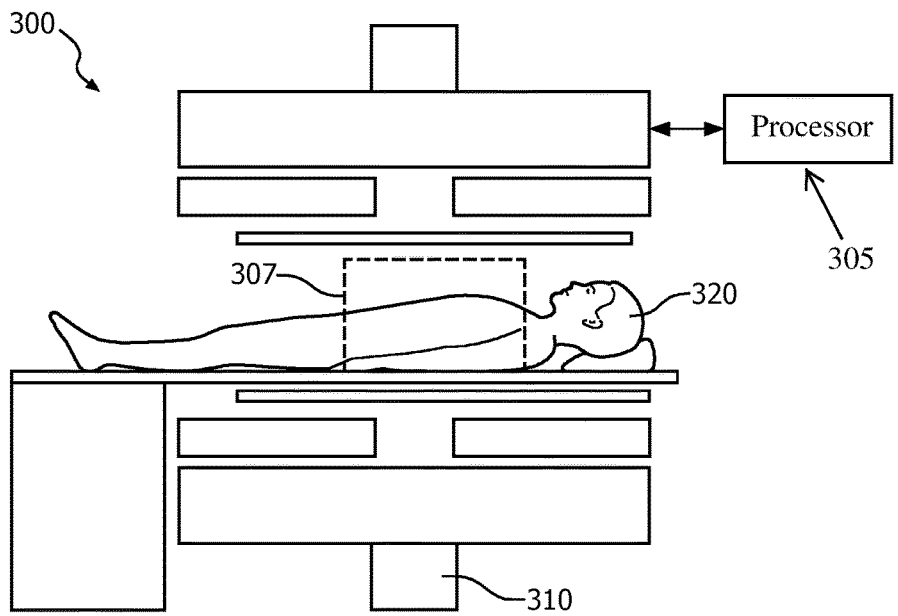

FIG. 3 diagrammatically shows a magnetic resonance imaging (MRI) system according to the invention. The MRI system 300 comprises a processor 305 for controlling the magnetic resonance imaging system to acquire MR data from a region of interest 307, wherein the processor is further configured for executing a computer program product which performs a method for tissue classification as herein described. The MRI system 300 could be combined with either one of a radiotherapy delivery 310 or PET system 310. The MRI system could be configured to use the tissue classification to create a radiotherapy plan. The MRI system could be configured to use the tissue classification for attenuation correction of a PET image.

Whilst the invention has been illustrated and described in detail in the drawings and foregoing description, such illustrations and description are to be considered illustrative or exemplary and not restrictive; the invention is not limited to the disclosed embodiments.

The invention claimed is:

1. A method, comprising:
   acquiring a first magnetic resonance image of a region of interest, wherein the first magnetic resonance image includes a first region and a second region, wherein the first region represents air and the second region represents bone;
   after acquiring the first magnetic resonance image, inducing a shape change in a portion of the region of interest which comprises air, or waiting for a shape change to happen in the portion of the region of interest which comprises air;
   after inducing the shape change in the portion of the region of interest which comprises air or waiting for the shape change to happen in the portion of the region of interest which comprises air, acquiring a second magnetic resonance image comprising the first region and the second region, wherein the first region has a different shape during the acquisition of the second magnetic resonance image compared to during the acquisition of the first magnetic resonance image;
   identifying the first region and the second region in the first magnetic resonance image and the second magnetic resonance image;
   comparing the first magnetic resonance image and the second magnetic resonance image with respect to the first region and the second region;
   classifying the first region of the first and second magnetic resonance images of the region of interest as representing air based on a presence of a shape difference of the first region between the first magnetic resonance image of the region of interest and the second magnetic resonance image of the region of interest; and
   classifying the second region of the first and second magnetic resonance images of the region of interest as representing bone based on an absence of a shape difference of the second region between the first magnetic resonance image of the region of interest and the second magnetic resonance image of the region of interest.

2. The method of claim 1, wherein the shape difference of the first region is caused by a shape change in a third region, wherein the third region comprises a tissue of a predetermined type, and wherein the third region is present in one or both of the first magnetic resonance image and the second magnetic resonance image.

3. The method of claim 2, further comprising inducing the shape change in the third region which comprises the tissue of the predetermined type between acquisition of the first magnetic resonance image and the second magnetic resonance image, wherein the shape change in the third region which comprises the tissue of the predetermined type further induces the shape change in the portion of the region of interest which comprises air.

4. The method of claim 1, further comprising using the classification of the first region and the classification of the second region to generate a pseudo computed tomography image and/or an attenuation map and/or a digitally reconstructed radiograph of the region of interest.

5. The method of claim 1, wherein the first magnetic resonance image the second magnetic resonance image are images of at least one of a head area and a neck area of a subject and wherein the shape difference is caused by a change in mucosa thickness.

6. The method of claim 1, comprising inducing the shape change in the portion of the region of interest which comprises air.

7. The method of claim 1, wherein the region of interest is in a subject, the method comprising inducing the shape change in the portion of the region of interest which comprises air by administering to the subject a drug which affects a thickness of mucosa which is present in the subject in the region of interest.

8. The method of claim 7, further comprising:
   classifying first pixels that change from a noise level intensity in the first magnetic resonance image to a standard mucosal signal level in the second magnetic resonance image as air pixels belonging to the first region representing air;
   applying a region growing algorithm to the classified first pixels in the first magnetic resonance image to identify all remaining pixels of the first region in the first magnetic resonance image; and
   classifying all remaining pixels which have a noise level intensity in the first magnetic resonance image as bone pixels belonging to the second region representing bone.

9. The method of claim 1, further comprising:
   classifying a third region as air when:

$$\frac{|V_{13} - V_{23}|}{0.5(V_{13} + V_{23})} > T$$

where $V_{13}$ is a volume of the third region in the first magnetic resonance image, $V_{23}$ is a volume of the third region in the second magnetic resonance image, and T is a threshold value; and
classifying a fourth region as bone when:

$$\frac{|V_{14} - V_{24}|}{0.5(V_{14} + V_{24})} < T$$

where $V_{14}$ is a volume of the fourth region in the first magnetic resonance image, and $V_{24}$ is a volume of the fourth region in the second magnetic resonance image.

10. The method of claim 1, wherein acquiring the first magnetic resonance image comprises performing a T1-enhanced three dimensional Cartesian fast-field echo acquisition, acquiring two signal echoes with a magnetization nearly out-phase at $TE_1=1.1$ ms and nearly in-phase at $TE_2=2.1$ ms.

11. A non-transitory computer readable medium having stored thereon program code for causing a computer to carry out steps of a method, wherein the method comprises:

receiving a first magnetic resonance image of a region of interest, wherein the first magnetic resonance image includes a first region and a second region, wherein the first region represents air and the second region represents bone;

receiving a second magnetic resonance image comprising the first region and the second region, wherein a shape of the first region is substantially different in the first image than in the second image, wherein a difference in the shape is caused by a change induced in the first region between acquisition of the first magnetic resonance image and acquisition of the second magnetic resonance image;

identifying the first region and second region in the first magnetic resonance image and the second magnetic resonance image;

comparing the first magnetic resonance image and the second magnetic resonance image with respect to the first region and the second region; and classifying the first region of the first and second magnetic resonance images of the region of interest as representing air based on a presence of a shape difference between the first magnetic resonance image of the region of interest and the second magnetic resonance image of the region of interest; and classifying the second region of the first and second magnetic resonance images of the region of interest as representing bone based on an absence of the shape difference between the first magnetic resonance image of the region of interest and the second magnetic resonance image of the region of interest.

12. The non-transitory computer readable medium of claim 11, wherein the first magnetic resonance image and the second magnetic resonance image are images of at least one of a head area and a neck area of a subject, and wherein the shape difference is caused by a change in mucosa thickness between the first magnetic resonance image and the second magnetic resonance image.

13. The non-transitory computer readable medium of claim 11, wherein the method further includes using the classification of the first region and the classification of the second region to generate a pseudo computed tomography image and/or an attenuation map and or a digitally reconstructed radiograph of the region of interest.

14. The non-transitory computer readable medium of claim 11, wherein the first magnetic resonance image and the second magnetic resonance image are T1 weighted DIXON images.

15. A magnetic resonance imaging system comprising a processor which is configured for executing the program code of the non-transitory computer readable medium of claim 11.

16. The magnetic resonance imaging (MRI) system of claim 15, further comprising a radiotherapy delivery system, wherein the magnetic resonance imaging system is configured to use the classification of the first region and the classification of the second region to create a radiotherapy plan for the radiotherapy delivery system.

17. The magnetic resonance imaging system of claim 15, further comprising a positron emission tomography (PET) system, wherein the magnetic resonance imaging system is configured to use the classification of the first region and classification of the second region for attenuation correction of a PET image of the PET system.

18. The magnetic resonance imaging system of claim 15, further comprising a body coil for signal transmission, and a 12-element phased-array posterior coil and a 16-element phased-array anterior coil for signal reception for producing magnetic resonance data from the region of interest, wherein the first magnetic resonance image and the second magnetic resonance image are based on magnetic resonance data.

* * * * *